United States Patent
Feng et al.

(10) Patent No.: US 10,702,524 B2
(45) Date of Patent: Jul. 7, 2020

(54) USE OF A COMPOUND IN REPAIRING NERVE INJURY

(71) Applicants: Shiqing Feng, Tianjin (CN); Xue Yao, Tianjin (CN)

(72) Inventors: Shiqing Feng, Tianjin (CN); Xue Yao, Tianjin (CN); Chao Sun, Tianjin (CN); Jian Hao, Tianjin (CN); Baoyou Fan, Tianjin (CN); Bo Li, Tianjin (CN); Huiquan Duan, Tianjin (CN); Chenxi Zhao, Tianjin (CN); Yan Zhang, Tianjin (CN); Xiaohong Kong, Tianjin (CN); Chang Liu, Tianjin (CN)

(73) Assignees: Shiqing Feng, Tianjin (CN); Xue Yao, Tianjin (CN)

( * ) Notice: Subject to any disclaimer, the term of this patent is extended or adjusted under 35 U.S.C. 154(b) by 0 days.

(21) Appl. No.: 16/478,751

(22) PCT Filed: Oct. 10, 2017

(86) PCT No.: PCT/CN2017/105571
§ 371 (c)(1),
(2) Date: Jul. 17, 2019

(87) PCT Pub. No.: WO2018/133457
PCT Pub. Date: Jul. 26, 2018

(65) Prior Publication Data
US 2019/0336501 A1 Nov. 7, 2019

(30) Foreign Application Priority Data
Jan. 23, 2017 (CN) .......................... 2017 1 0050876

(51) Int. Cl.
*A61K 31/505* (2006.01)
*A61P 25/00* (2006.01)
(52) U.S. Cl.
CPC ............ *A61K 31/505* (2013.01); *A61P 25/00* (2018.01)
(58) Field of Classification Search
CPC .............................. A61K 31/505; A61P 25/00
USPC ....................................................... 514/256
See application file for complete search history.

(56) References Cited
U.S. PATENT DOCUMENTS
2016/0297748 A1 10/2016 Stockwell et al.

FOREIGN PATENT DOCUMENTS

| CN | 106822136 A | 6/2017 | | |
|---|---|---|---|---|
| WO | WO 2013/152039 | 10/2013 | | |
| WO | WO 2015/084749 | 6/2015 | | |
| WO | WO-2015084749 A1 | * 6/2015 | ........... | C07D 213/38 |

OTHER PUBLICATIONS

Hofmans, et al.; "Novel Ferroptosis Inhibitors with Improved Potency and ADME Properties"; Journal of Medicinal Chemistry; vol. 59, pp. 2041-2053 (2016).
Linkermann, et al.; "Synchronized renal tubular cell death involves ferroptosis"; PNAS; vol. 111, No. 47, pp. 16836-16841 (Nov. 25, 2014).
Wang, Zhongcheng; "Neurosurgery"; pp. 857-859 (2015).

* cited by examiner

*Primary Examiner* — Yong L Chu
(74) *Attorney, Agent, or Firm* — James S. Keddie; Bozicevic, Field & Francis LLP (57) ABSTRACT

The present invention falls within the field of medical technology, and in particular relates to the use of a compound as shown in formula (I). In particular, the present invention relates to the use of the compound as shown in formula (I) in the preparation of a pharmaceutical composition for preventing and/or treating a nerve injury, or relieving a nerve injury-associated symptom, and further relates to the use thereof in the preparation of a healthcare product for protecting an injured nerve and/or improving motor function. After a nerve injury has occurred, the compound can reduce the production of pro-inflammatory cytokine, decrease the level of apoptosis, promote the survival of neuron, inhibit the formation of glial scar, and has a significant effect in promoting the recovery of motor function.

Formula (I)

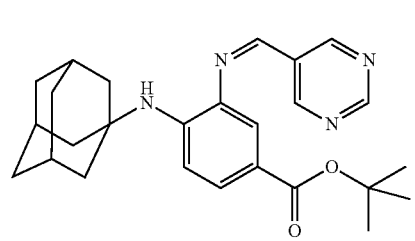

5 Claims, 6 Drawing Sheets

USE OF A COMPOUND IN REPAIRING NERVE INJURY

CROSS-REFERENCE TO RELATED APPLICATIONS

This application is a § 371 national phase of International Application No. PCT/CN2017/105571, filed on Oct. 10, 2017, which claims the benefit of Chinese Patent Application Serial No. 201710050876.0, filed on Jan. 23, 2017, which applications are incorporated by reference herein.

TECHNICAL FIELD

The invention is in the field of medical technology. In particular, the invention relates to the use of a compound of formula (I), and particularly, to the use of a compound of formula (I) in manufacture of a medicament for preventing and/or treating a nerve injury.

BACKGROUND ART

Spinal cord injury (SCI) is a severe traumatic disease with high incidence and high disability rate, and repairing the injury always is a difficult problem in international medical community. Due to deficiencies in effective repairing solutions, only less than 1% patients suffered from the SCI have achieved complete recovery of nerve functions.

The spinal cord injuries include primary injuries and secondary injuries. The primary injuries are caused by mechanical compression, bleeding, electrolyte outflow and other factors. The primary spinal cord injuries occur at the moment of being injured, and the injuries are irreversible. However, the scope of the primary injuries is limited. The secondary spinal cord injuries undergo an evolution process that will go on from hours to days and the injuries re reversible. The main injury mechanism of the spinal cord injuries is concerned to secondary injuries after being injured. At present, it has been found that the secondary spinal cord injury process is a complex pathological process in which multiple signaling pathways are involved and a considerable degree of cascade amplifications and cross reactions are present, and thus it has complex regulating mechanisms. Some studies are made to demonstrate that there are complex and diverse factors that will affect regenerations of neurons and axons after injury, including vascular injuries, oxygen free radical release, inflammation overreaction, electrolyte imbalance (e.g., intracellular calcium overload), and abnormal energy metabolism. Additionally, pathological changes after injury are mainly reflected by changes of microenvironment of the injury site and its surrounding. After spinal cord injury, a series of immunocompetent cells, including neutrophils and activated macrophages, can be recruited around the spinal cord tissues. These cells can produce many pro-inflammatory chemokines/cytokines, such as TNFα, IL-1β, thereby to aggravate the spinal cord injury. In the acute stage, severe inflammatory reactions will result in apoptosis of a large number of cells, which eventually result in formation of local void. In the chronic stage, glial cells migrate into the void and proliferate, to repair the void defect, which results in formation of glial scar. The glial scar hinders the extension of regenerated axons to distal ends, and ultimately, this will seriously affect long-term functional recovery. This change in the pathological environment will largely determine the severity of the final injury, and will greatly influence the repairing effects of interventions. At present, there is no systematic and complete mechanism theory to explain the influences of the pathological environment. Since the exact injury mechanism of the spinal cord injury is not explicit, it is difficult to perform corresponding targeted treatments, and thus the achieved treating effects are not ideal.

SUMMARY OF THE INVENTION

In the invention, unless being otherwise specified, the scientific and technical terms used herein have meanings as generally understood by those skilled in the art. Moreover, the laboratory operation steps involved here each are conventional steps that are widely used in the art. At the same time, in order to better understand the invention, the definitions and explanations of the related terms are provided below.

In the invention, the compound of the formula (I) has a structure as shown below:

The compound of the formula (I) may be synthesized according to the method as provided by Andreas Linkermann et al. (PNAS, vol. 111, no. 47, 2014).

The inventors of the invention surprisingly find out that the compound of the formula (I) can reduce nerve injuries, especially, reduce production of pro-inflammatory cytokines (such as TNFα, IL-1β and ICAM1) as caused by spinal cord injuries, reduce level of cell apoptosis, reduce formation of glial scar, increase survival rates of neurons and oligodendrocytes, and achieve functional repairs of nerve injuries. So, the following inventions are provided:

In one aspect, the invention is provided with use of a compound of the formula (I) in manufacture of a pharmaceutical composition for treating and/or preventing a nerve injury.

In one aspect, the invention is further provided with use of a compound of the formula (I) in manufacture of a pharmaceutical composition for relieving a symptom related to a nerve injury.

In one aspect, the invention is provided with use of a compound of the formula (I) in manufacture of a health-care product for protecting an injured nerve and/or improving motor function.

In one aspect, the invention is provided with a compound of the formula (I) that is useful for treating and/or preventing a nerve injury in a patient or subject, or for relieving a symptom related to a nerve injury in a patient or subject, or for protecting an injured nerve and/or improving motor function in a patient or subject.

In one aspect, the invention is provided with a method of treating and/or preventing a nerve injury, or a method of relieving a symptom related to a nerve injury, or a method for protecting an injured nerve and/or improving motor function, comprising administrating an effective amount of the compound of the formula (I) to a patient or subject in need thereof.

In some embodiments, the nerve injury is a central nerve injury. In some embodiments, the nerve injury is brain injury or spinal cord injury. In some embodiments, the nerve injury is acute or chronic spinal cord injury.

In some embodiments, the nerve injury is caused by a violence factor, mechanical compression, bleeding, electrolyte outflow, and/or ischemic reperfusion.

In some embodiments, the symptom related to a nerve injury is selected from the group of pro-inflammatory factor production, inflammation, glial scar formation, death and/or apoptosis of neurons and/or oligodendrocytes, and loss and/or decline of motor function.

In some embodiments, the pharmaceutical composition or the health-care product comprises an effective amount of the compound of the formula (I) and a pharmaceutically acceptable excipient. In some embodiments, the pharmaceutical composition or the health-care product comprises an effective amount of the compound of the formula (I) and a carrier, e.g., a pharmaceutically acceptable carrier. Carriers can be used in the invention include, but are not limited to, ion exchangers, alumina, aluminum stearate, lecithin, serum proteins such as human serum protein, buffer substances such as phosphoric acid salts, glycerin, sorbic acids, potassium sorbate, partial glyceride mixtures of saturated plant fatty acids, water, salt or electrolytes, for example such as protamine sulfate, disodium hydrogen phosphate, potassium hydrogen phosphate, sodium chloride, zinc salts, colloidal silica, magnesium trisilicate, polyvinylpyrrolidone, celluloses, polyethylene glycol, sodium carboxymethyl cellulose, polyacrylates, beeswax, polyethylene-polyoxypropylene block polymers and lanolin.

The pharmaceutical composition or health-care product of the invention can be made into any dosage forms, for example any one of pharmaceutically acceptable dosage forms, such as oral dosage forms or non-oral dosage forms, such as tablets, capsules, powder, pills, granules, solutions, suspensions, syrups, injections (including injection liquids, sterile powder for injection and concentrated solutions for injection), suppositories, inhalants or sprays.

The pharmaceutical composition or health-care product of the invention can be administrated to patents or subjects in need thereof in any suitable ways, such as oral, parenteral, rectal, pulmonary or local administrations. When being used for oral administration, the pharmaceutical composition or the health-care product can be made into oral formulations, for example, oral solid formulations such as tablets, capsules, pills, granules, etc., or oral liquid formulations such as oral solutions, oral suspensions, syrup, etc. When being made into oral formulations, the pharmaceutical composition or the health-care product may additionally comprise suitable fillers, adhesives, disintegrants, and lubricants. When being used for parenteral administration, the pharmaceutical composition or the health-care product can be made into injections, including injection liquids, sterile powder for injection and concentrated solutions for injection. When being made into injections, the pharmaceutical composition or the health-care product may be produced by using conventional methods in the field of medicine manufacture. When the injections are formulated, to the pharmaceutical composition or the health-care product, additives may not be added or suitable additives are added according to medicine properties. When being used for rectal administration, the pharmaceutical composition or the health-care product can be made into suppositories, et al. When being used for pulmonary administration, the pharmaceutical composition or the health-care product can be made into inhalants or sprays.

In some embodiments, the health-care product of the invention is a dietary supplement. The dietary supplement of the invention is meant to a food product having specific health-care function, i.e., a food product suitable for specific populations to eat and having body-regulating functions. In some embodiments, said dietary supplement is not intended for disease treatments.

In some preferred embodiments, the compound is present in the pharmaceutical composition or the health-care product in effective amount for disease prevention and/or disease treatment. In some preferred embodiments, the compound is present in the pharmaceutical composition or the health-care product in a form of unit dose.

The "effective amount" of the invention refers to an amount that is sufficient to achieve or at least partially achieve desirable effects. For example, the "effective amount for disease prevention" refers to an amount that is sufficient to prevent, hinder or retard occurrence of a disease; the "effective amount for disease treatment" refers to an amount that is sufficient to heal or at least partially hinder a disease or a complication thereof in a patient suffered therefrom. Measurement of such an effective amount is entirely within the abilities of a person skilled in the art. For example, an effective amount for therapeutic uses depends on severity of the disease to be treated, overall states of the patient's immune systems, patient's common conditions, such as age, weight and sexuality, administration means of the medicine, and other treatment that perform simultaneously.

In the invention, the patient or subject includes a vertebrate, for example, a mammal such as a bovine, equid, caprid, suidae, canine, feline, rodent, and primate, e.g., a human.

BENEFICIAL EFFECTS OF THE INVENTION

Through a therapeutic experiment on spinal cord injury modeling animals, it is found that the compound of the formula (I) can reduce production of pro-inflammatory cytokines, decrease apoptosis level of neurons, promote survival of neurons, reduce formation of glial scar, promote survival rates of neurons, inhibit formation of glial scar, and significantly improve BBB score of animals after treatment, which show that the compound of the formula (I) has significant effect of promoting the recovery of motor function after nerve injuries.

In order to make the objects, technical solutions and advantages of the invention clearer, the invention is further described in detail in connection with the drawings and the examples. It should be understood that the following examples are used only to illustrate the invention, but are not regarded to limit the scope of the invention. Examples with specific conditions that are not specified should be carried out in accordance with conventional conditions or conditions recommended by the manufacturer. The reagents or devices used here with the manufacturers not being specified are conventional products that are commercially available.

DESCRIPTIONS TO THE DRAWINGS OF THE INVENTION

SPECIFIC MODES FOR CARRYING OUT THE INVENTION

Example 1: Establishment of Spinal Cord Injury Animal Model of Rats

Figure 1:
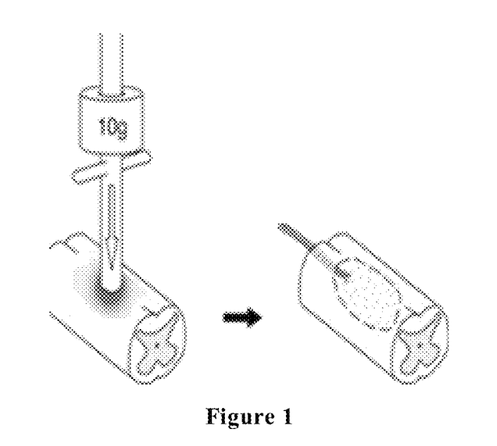
FIG. 1 is a schematic diagram of establishing a rat spinal cord injury model, wherein the exposed rat spinal cord segment is fixed on a striking device, with a striking strength of 10 g weight.

Animal models of acute spinal cord injury experiment were established by using an IMPACTOR MODEL-II spinal cord injury striking system. Sixty female Wistar rats with the age from 8 to 10 weeks and the weight from 230 to 250 g were divided into three groups with 20 rats in each group: a sham-surgery operated group, a control group (spinal cord injury group) and an experimental group, respectively. At 15 minutes before striking injury, the rats in the experimental group were injected with the compound of the formula (I) at a dose of 15 mg/kg body weight. After the rats were anaesthetized, they were surgically resected with the $10^{th}$ thoracic vertebral lamina, and the corresponding spinal cord segment was exposed and fixed under a striking device, wherein the weight of the striking device had a striking strength of 10 g and a diameter of 2.5 mm, and dropped from a height of 25 mm (10 g×25 mm) (as shown in FIG. 1). After being striking, the rats exhibited local edema and hyperemia in the injured spinal cords, ephemeral spasmodic jerk of the rear limbs, and paralysis of both lower limbs after tail swing, and the BBB scores were 0 at the day after injury occurred, all of which indicated that the models were successfully established.

Example 2: Impacts of Compound of the Formula (I) on Inflammation at Spinal Cord Injury Sites At 6 hours, 24 hours, 48 hours, 7 days, 14 days, and 28 days after injury, respectively, the rat spinal cord tissues were sampled for the Western Blot test, so as to test the inhibiting function of the compound of the formula (I) against the pro-inflammatory cytokines at the spinal cord injury sites.

1. ICAM1 Expression

Figure 2:
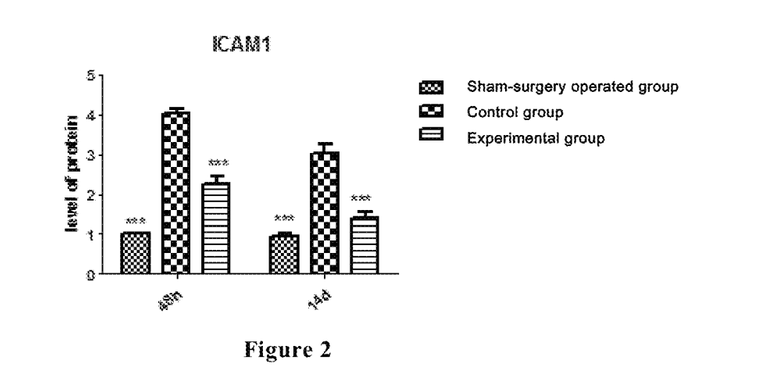
FIG. 2 shows the ICAM1 expressions of the spinal cord tissues of the rats in a sham-surgery operated group, a control group and an experimental group at 48 hours and 2 weeks after spinal cord injury, and in the figure, the relative expression quantity of ICAM1 is the longitudinal coordinate, and the time is the horizontal coordinate. The results as shown in the figure are obtained by Western Blot test and gray level analysis.

Through Western Blot analysis, it has been found that at 48 hours after injury, the ICAM1 of the control group was highly expressed as compared to that of the sham-surgery operated group. However, when the compound of the formula (I) was employed to intervene, the ICAM1 expression of the experimental group was significantly decreased. Through gray level analysis, it was found that the relative expression quantity of the ICAM1 of the experimental group was significantly reduced as compared to the control group (see FIG. 2).

Through Western Blot analysis, it has been found that at 2 weeks after injury, the ICAM1 of the control group was still in a high expression state as compared to the sham-surgery operated group, whereas the ICAM1 expression of the experimental group was significantly decreased. Through gray level analysis, it was found that the relative expression quantity of the ICAM1 of the experimental group was significantly reduced as compared to that of the control group (see FIG. 2).

2. TNF-α Expression

Figure 3:
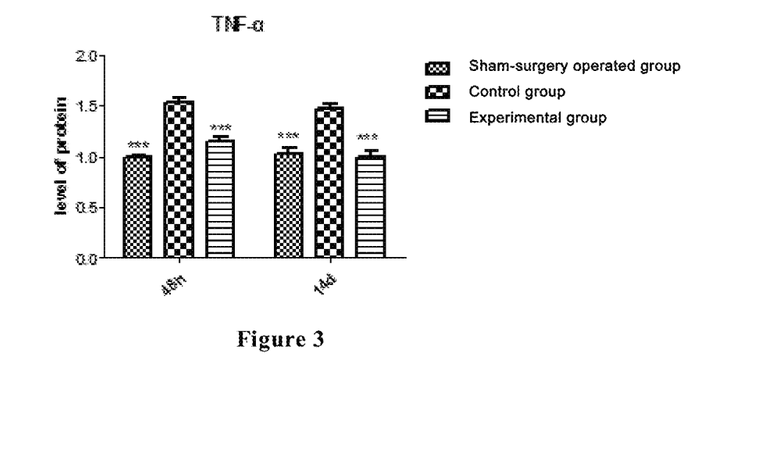
FIG. 3 shows the TNF-α expressions of the spinal cord tissues of the rats in a sham-surgery operated group, a control group and an experimental group at 48 hours and 2 weeks after spinal cord injury, and in the figure, the relative expression quantity of TNF-α is the longitudinal coordinate, and the time is the horizontal coordinate. The results as shown in the figure are obtained by Western Blot test and gray level analysis.

Through Western Blot analysis, it has been found that at 48 hours after injury, the TNF-α of the control group was highly expressed as compared to that of the sham-surgery operated group, whereas the TNF-α expression of the experimental group was decreased, close to the level of the shame-surgery operated group. Through gray level analysis, it was found that the relative expression quantity of the TNF-α of the experimental group was reduced as compared to the control group (see FIG. 3).

Through Western Blot analysis, it has been found that at 2 weeks after injury, the TNF-α of the control group was in a high expression state as compared to the sham-surgery operated group, whereas the TNF-α expression of the experimental group was significantly decreased. Through gray level analysis, it was found that the relative expression quantity of the TNF-α of the experimental group was significantly reduced as compared to that of the control group (see FIG. 3).

3. IL-1β Expression

Figure 4:
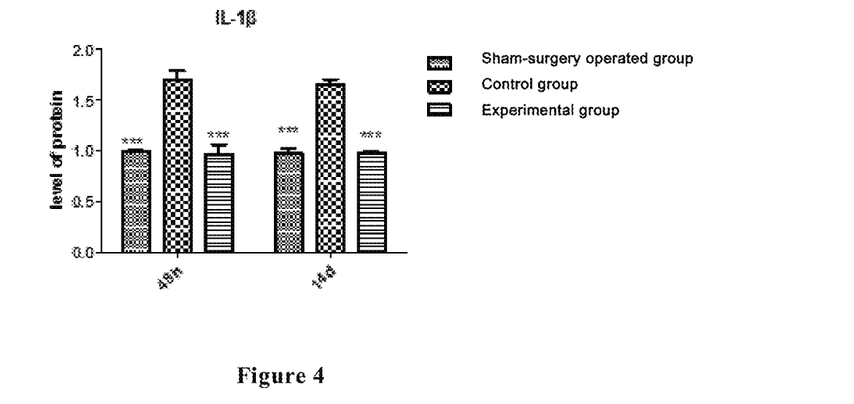
FIG. 4 shows the IL-1β expressions of the spinal cord tissues of the rats in a sham-surgery operated group, a control group and an experimental group at 48 hours and 2 weeks after spinal cord injury, and in the figure, the relative expression quantity of IL-1β is the longitudinal coordinate, and the time is the horizontal coordinate. The results as shown in the figure are obtained by Western Blot test and gray level analysis.

Through Western Blot analysis, it has been found that at 48 hours after injury, the IL-1β of the control group was highly expressed as compared to that of the sham-surgery operated group, whereas the IL-1β expression of the experimental group was significantly decreased, close to the level of the shame-surgery operated group. Through gray level analysis, it was found that the relative expression quantity of the IL-1β of the experimental group was reduced as compared to the control group (see FIG. 4).

Through Western Blot analysis, it has been found that at 2 weeks after injury, the IL-1β of the control group was in a high expression state as compared to the sham-surgery operated group, whereas the IL-1β expression of the experimental group was significantly decreased. Through gray level analysis, it was found that the relative expression quantity of the IL-1β of the experimental group was significantly reduced as compared to that of the control group (see FIG. 4).

The above experimental results show that as compared to the control group, the compound of the formula (I), can significantly reduce the expression level of the pro-inflammatory cytokine at the spinal cord injury sites of the rats at the acute stage of the spinal cord injury, so as to reduce inflammations.

Example 3: Impacts of Compound of the Formula (I) on Cell Apoptosis after Spinal Cord Injury At 6 hours, 24 hours, 48 hours, 7 days, 14 days, 28 days and 56 days after injury, respectively, the rat spinal cord tissues were sampled for the Western Blot test and TUNEL staining, so as to test the inhibiting function of the compound of the formula (I) against the cell apoptosis at the spinal cord injury sites.

1. Caspase 3 Expression

Figure 5:
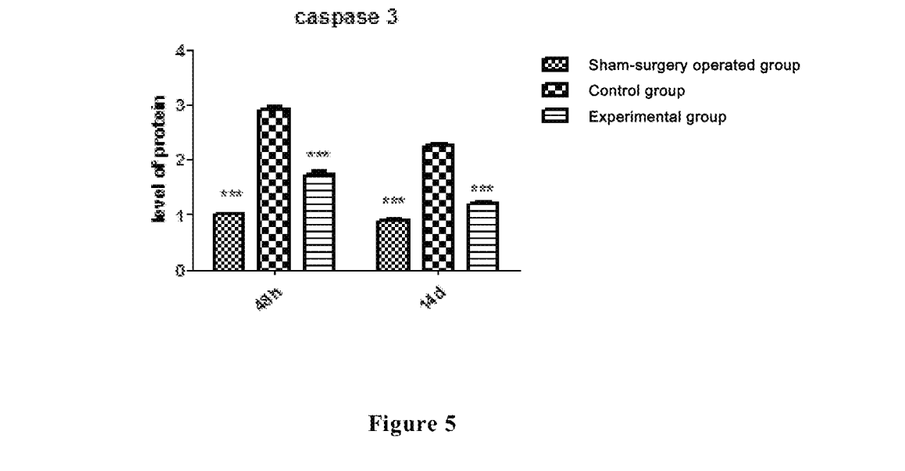
FIG. 5 shows the Caspase 3 expressions of the spinal cord tissues of the rats in a sham-surgery operated group, a control group and an experimental group at 48 hours and 2 weeks after spinal cord injury, and in the figure, the relative expression quantity of Caspase 3 is the longitudinal coordinate, and the time is the horizontal coordinate. The results as shown in the figure are obtained by Western Blot test and gray level analysis.

Through Western Blot analysis, it has been found that at 48 hours after injury, the Caspase 3 of the control group was highly expressed as compared to that of sham-surgery operated group, whereas the Caspase 3 expression of the experimental group was significantly decreased. Through gray level analysis, it was found that the relative expression quantity of the Caspase 3 of the experimental group was reduced as compared to that of the control group (see FIG. 5).

Through Western Blot analysis, it has been found that at 2 weeks after injury, the Caspase 3 of the control group was still in a high expression state as compared to the shame-surgery operated group, whereas the Caspase 3 expression of the experimental group was significantly decreased. Through gray level analysis, it was found that the relative expression quantity of the Caspase 3 of the experimental group was significantly reduced as compared to that of the control group (see FIG. 5).

2. TUNEL Staining

Figure 6:
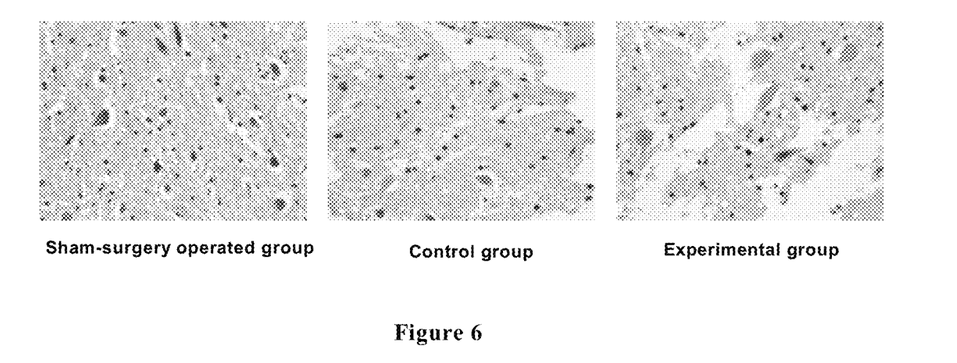
FIG. 6 shows the results of TUNEL staining of the spinal cord tissues of the rats in each group at 48 hours after spinal cord injury.

At 48 hours after injury, TUNEL staining was performed on three groups of spinal cord tissues. TUNEL-stained positive cells were located in the gray matter and white matter of the spinal cords, and the cell nuclei was stained brown-yellow and mostly distributed in the center of the injure and the margin thereof. Moreover, the brown-yellow particles in the gray matter were less than those in the white matter, and they would involve characteristic apoptotic changes, for example, hyperchromatic cytoplasm and apoptotic cell chromatin pyknosis, which were gathered around nuclear membrane in a plaque form. The quantity of the stained positive particles of the control group was significantly higher than that of the control group, and the corresponding difference in the quantity of the positive cells had a statistical significance ($p<0.05$) (see FIG. 6).

The above experimental results showed that as compared to the control group, the compound of the formula (I) can significantly reduce the cell apoptosis at the spinal cord injury sites of rats at the acute stage of the spinal cord injury.

Figure 7:
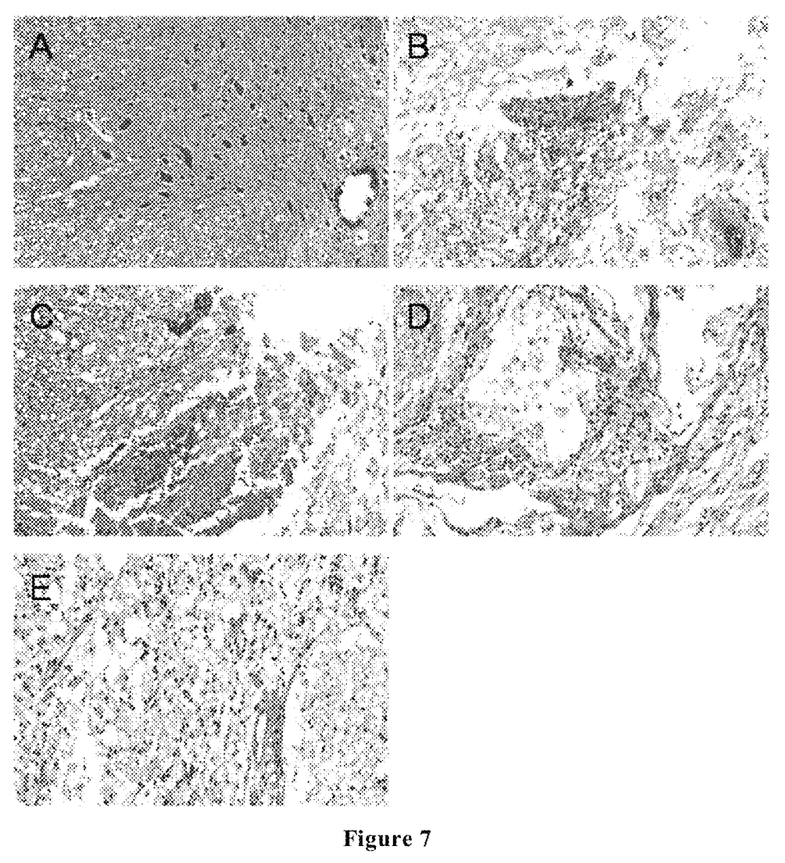
FIG. 7 shows the HE staining of the spinal cord tissues of the rats in each group at 2 day and 8 weeks after spinal cord injury, wherein Figure A shows the results of the sham-surgery operated group at 48 hours (200×); Figure B shows the results of the control at 48 hours (200×); Figure C shows the results of the experimental group at 48 hours (200×); Figure D shows the results of the control group at 8 weeks (200×); and Figure E shows the results of the experimental group at 8 weeks (200×).

Example 4: Impacts of Compound of the Formula (I) on Formation of Void and Glial Scar after Spinal Cord Injury 1. Comparing the Areas of Void and Glial Scar after Spinal Cord Injury by the Means of HE Staining FIG. 7 showed the results of observations and evaluations on the HE staining results of the three groups of spinal cord tissues after injury. At 48 hours after injury, the tissues were observed at high magnification (200×). No spinal cord structure destroy was observed on the rats in the sham-surgery operated group. In the control group, significant changes occurred, mainly including hemorrhage, infiltration with a large number of inflammatory cells and spinal cord structural disorder, and it was observed that in grey matter, a large number of cells were lost, while in the white matter, significant swelling of neurites was observed and axonal terminals were in sphere. The interventions with the compound of the formula (I) could significantly alleviate the above series of changes. The histopathological scores showed that the comparisons of the control group and experimental group with the shame-surgery operated group had significant differences, whereas the comparison between the control group and the experimental group did not have statistical significance.

At 8 weeks after spinal cord injury, with the HE staining, it was observed that large-area voids left over in the control group, and the area was significantly increased as compared to that in the experimental group, with statistical significance (p<0.05). At the same time, at high magnification, infiltration with a large number of inflammatory cells was observed in the control group, while in the experimental group, the inflammatory cells were significantly reduced.

Figure 8:
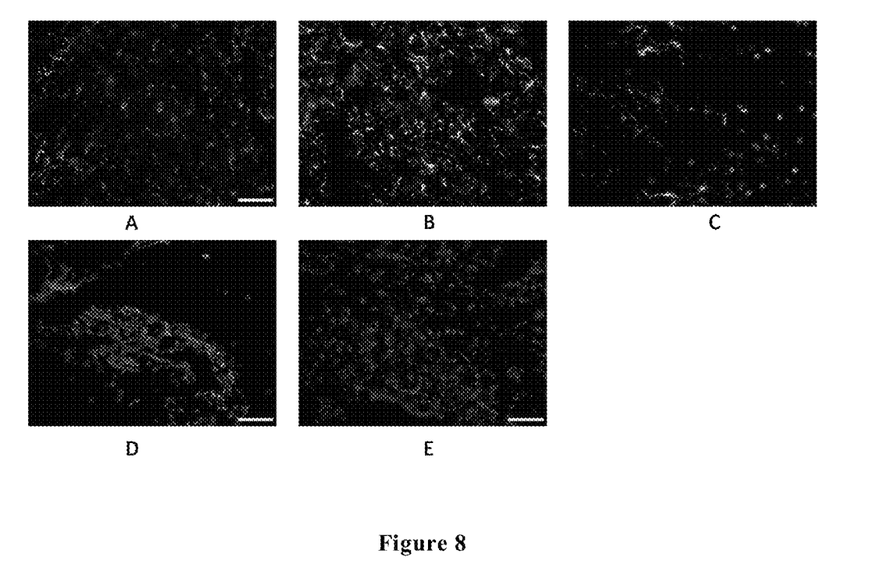
FIG. 8 shows the immunofluorescence (DAPI+GFAP) results (400×) of the spinal cord tissues of the rats in each group at 48 hours and 2 weeks after spinal cord injury, wherein Figure A shows the immunofluorescence results of the sham-surgery operated group at 48 hours; Figure B shows the immunofluorescence results of the control group at 48 hours; Figure C shows the immunofluorescence results of the experimental group at 48 hours; Figure D shows the immunofluorescence results of the control group at 2 weeks; and Figure E shows the immunofluorescence results of the experimental group at 2 weeks.

2. Testing Glial Fibrillary Acidic Protein (GFAP) Expression by Frozen-Section Immunofluorescence Histochemical Method At 48 hours after injury, the spinal cord tissues were subjected to GFAP immunofluorescent staining. In the shame-surgery operated group, it was observed that red fluorescence (GFAP) was less and distributed uniformly; in the control group, a large quantity of red fluorescence may be observed in the injured areas, which showed that a large quantity of star-shaped glial cells were proliferated and gathered; in the experimental group, only a little of red fluorescence was observed, which showed that only mild start-shaped glial cell proliferation occurred, and the quantity of the formed glial scars was significantly decreased as compared to the control group, and the corresponding difference had a statistical significance (p<0.05).

At 2 weeks after surgery, the GFAP fluorescence of the control group was still stronger than the experimental group (p<0.05) (see FIG. 8).

The above experimental results showed that as compared to the control group, the compound of the formula (I), can significantly reduce formations of void and glial scar after spinal cord injury.

Figure 9:
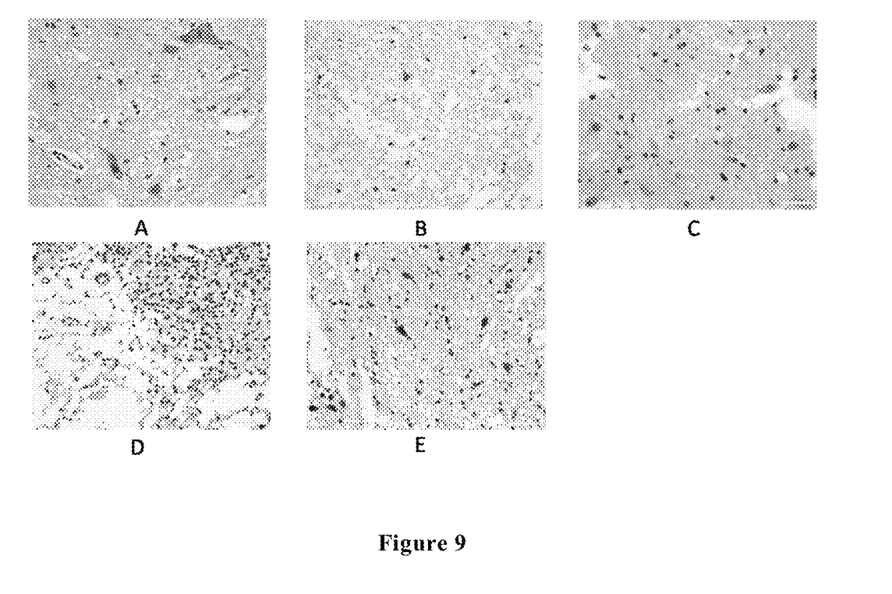
FIG. 9 shows the NEUN immunohistochemical results of the spinal cord tissues of the rats in each group at 48 hours and 2 weeks after spinal cord injury, wherein Figure A shows the immunohistochemical results of the sham-surgery operated group at 48 hours; Figure B shows the immunohistochemical results of the control group at 48 hours; Figure C shows the immunohistochemical results of the experimental group at 48 hours; Figure D shows the immunohistochemical results of the control group at 2 weeks; and Figure E shows the immunohistochemical results of the experimental group at 2 weeks.

Example 5: Impacts of Compound of the Formula (I) on Survival Rates of Neurons and Oligodendrocytes At 48 hours and 2 weeks after injury, respectively, the three groups of rat spinal cord tissues were subjected to NEUN immunohistochemical staining. The staining results showed that the shame-surgery operated group exhibited a large quantity of NEUN(+) neuron cells; the tissues in the control group broke and no obvious NEUN(+) neuron cells appeared; in the experimental group, the tissues broke, and in the tissues, a middle quantity of NEUN(+) neuron cells were present. As compared to the control group, more positive cells were present in the experimental group, and the corresponding difference had a statistical significance (p<0.05) (see FIG. 9). The results showed that the survival rate of neuron cells in the experimental group was higher than that in the control group.

Figure 10:
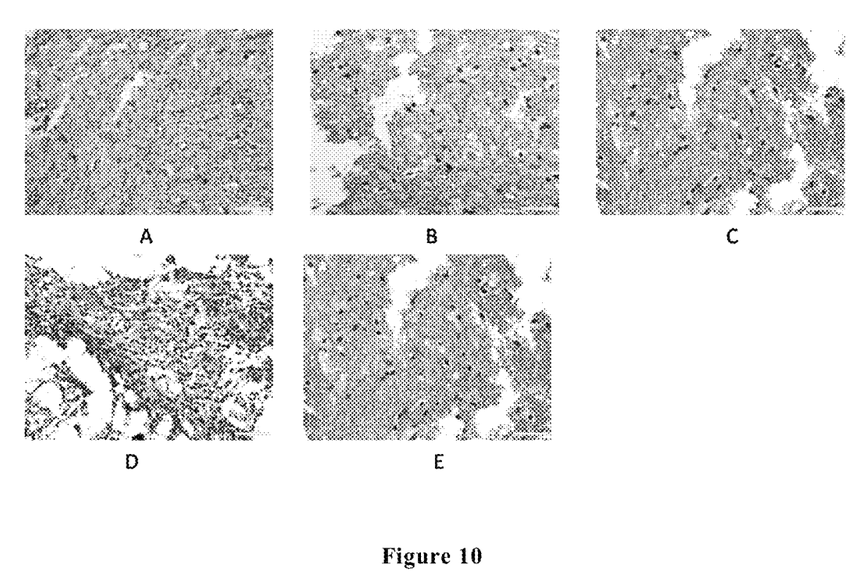
FIG. 10 shows the CNpase immunohistochemical results of the spinal cord tissues of the rats in each group at 48 hours and 2 weeks after spinal cord injury, wherein Figure A shows the immunofluorescence results of the sham-surgery operated group at 48 hours; Figure B shows the immunofluorescence results of the control group at 48 hours; Figure C shows the immunofluorescence results of the experimental group at 48 hours; Figure D shows the immunofluorescence results of the control group at 2 weeks; and Figure E shows the immunofluorescence results of the experimental group at 2 weeks.

At 48 hours and 2 weeks after injury, respectively, the three groups of spinal cord tissues were subjected to CNpase immunohistochemical staining. The staining results showed that at 48 hours, the shame-surgery operated group had uniformly distributed CNpase positive regions and more positive areas; in the control group and in the experimental control, the tissues broke, and the CNpase positive area did not markedly differ from that in the shame-surgery operated group. At 2 weeks after injury, the CNpase positive regions in the control group significantly decreased, and the CNpase positive regions in the experimental group were uniformly distributed; the experimental control, as compared to the control group, had a larger positive area and more positive cells, and the corresponding differences had statistical significance (p<0.05) (see FIG. 10). The results showed that the survival rate of the oligodendrocytes in the experimental group was higher than that in the control group.

The above experimental results showed that as compared to the control group, the compound of the formula (I) could significantly reduce death of neurons and oligodendrocytes and increase their survival rates after spinal cord injury.

Example 6: Impacts of Compound of the Formula (I) on Repair of Motor Function of Rats after Spinal Cord Injury Motor function of rear limbs of the tested animals were evaluated by scoring with BBB (Basso Beattie Bresnahan locomotor rating scale, BBB). The BBB scoring was one of internationally recognized objective standards regarding nerve functions of rats after spinal cord injury. In the project, the motor function of rear limbs of the rats was evaluated from 1 day before injury to 8 weeks after injury by double-blind independent observations and records with two persons and finally statistical analyses.

Figure 11:
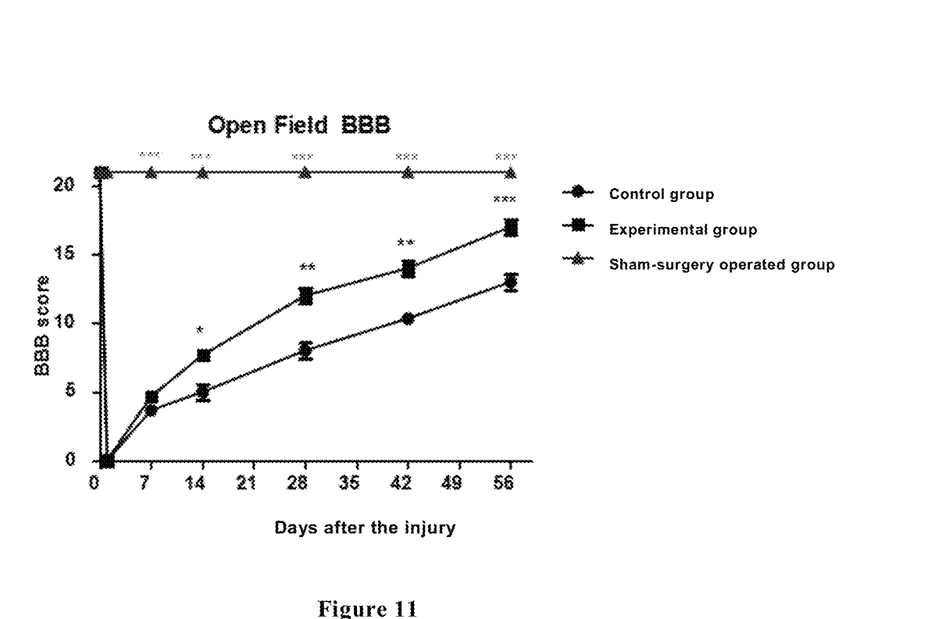
FIG. 11 shows BBB scores of the rats in each group in the respective time periods after injury.

FIG. 11 showed the BBB score of each group at different time points after injury. At 48 hours after injury, the comparisons of the control group and the experimental group with the shame-surgery operated group had significant statistical differences (p<0.01), and the comparison between the experimental group and the control group did not have any statistical significance (p>0.05); at 1 week after injury, the BBB scoring was performed, wherein the comparisons of the control group and the experimental group with the shame-surgery operated group had significant statistical differences (p<0.01), and the comparison between the experimental group and the control group did not have any statistical significance (p>0.05); at 2 weeks after injury, the BBB scoring was performed, wherein the comparisons of the control group and the experimental group with the shame-surgery operated group had significant statistical differences (p<0.01), and the comparison between the experimental group and the control group also had a statistical significance (p<0.05); at 8 weeks after injury, the BBB scoring was performed, wherein the comparisons of the control group and the experimental group with the shame-surgery operated group had significant statistical differences (p<0.01), and the comparison between the experimental group and the control group also had a statistical significance (p<0.01).

As seen from FIG. 11, the BBB score of the experimental group that was treated with the compound of the formula (I), at 8 weeks after injury, was significantly higher than that of the control group, and this showed that the treatment with the compound of the formula (I) could significantly promote motor function recovery of rats after spinal cord injury.

The above examples are only the preferred examples in the invention, and they are not used for limiting the scope of the invention; without deviation of the spirit and scope of the invention, amendments or equivalent substitutions to the invention should be covered in the protection scope of the claims in the invention.

The invention claimed is:

1. A method of relieving a symptom related to a nerve injury, comprising administrating an effective amount of a compound of the formula (I) to a patient or subject in need thereof:

wherein the symptom related to a nerve injury is selected from the group consisting of: production of pro-inflammatory factor, inflammation, formation of glial scar, death or apoptosis of neuron and/or oligodendrocyte; wherein the nerve injury is an acute spinal cord injury caused by a violence factor.

2. The method of claim 1, wherein the patient or subject is a vertebrate.

3. The method of claim 1, wherein the patient or subject is a mammal.

4. The method of claim 1, wherein the patient or subject is a bovine, equid, caprid, suidae, canine, feline, rodent or primate.

5. The method of claim 1, wherein the patient or subject is a human.

* * * * *